United States Patent [19]
Jeffrey

[11] Patent Number: 5,957,897
[45] Date of Patent: Sep. 28, 1999

[54] HOLLOW NEEDLE APPLICATOR FOR CARTRIDGED DRUGS

[75] Inventor: Peter Jeffrey, Liverpool, United Kingdom

[73] Assignee: Safe-T-Limited, Isle of Man, United Kingdom

[21] Appl. No.: 08/750,710

[22] PCT Filed: Jun. 16, 1995

[86] PCT No.: PCT/GB95/01418

§ 371 Date: Feb. 26, 1997

§ 102(e) Date: Feb. 26, 1997

[87] PCT Pub. No.: WO95/35126

PCT Pub. Date: Dec. 28, 1995

[30] Foreign Application Priority Data

Jun. 17, 1994 [GB] United Kingdom .................. 9412301

[51] Int. Cl.[6] ............................................... A61M 5/315
[52] U.S. Cl. ........................ 604/223; 604/110; 604/195; 604/187; 604/232
[58] Field of Search .................................. 604/110, 134, 604/195, 135, 187, 192, 193, 196, 221–234, 136, 157

[56] References Cited

U.S. PATENT DOCUMENTS

| | | |
|---|---|---|
| 2,888,924 | 6/1959 | Dunmire . |
| 3,712,301 | 1/1973 | Sarnoff ................................ 128/218 A |
| 3,797,489 | 3/1974 | Sarnoff ................................ 128/218 F |
| 4,664,653 | 5/1987 | Sagstetter et al. ....................... 604/197 |
| 4,678,461 | 7/1987 | Mesa ........................................ 604/157 |
| 5,092,843 | 3/1992 | Monroe et al. ........................... 604/138 |
| 5,102,393 | 4/1992 | Sarnoff et al. ........................... 604/136 |
| 5,176,643 | 1/1993 | Kramer et al. ........................... 604/135 |
| 5,300,030 | 4/1994 | Crossman et al. ....................... 604/136 |
| 5,330,430 | 7/1994 | Sullivan .................................. 604/134 |
| 5,354,286 | 10/1994 | Mesa et al. .............................. 604/230 |
| 5,665,071 | 9/1997 | Wyrick .................................... 604/134 |
| 5,679,111 | 10/1997 | Hjertman et al. ........................ 604/135 |
| 5,695,472 | 12/1997 | Wyrick .................................... 604/136 |

Primary Examiner—Corrine McDermott
Assistant Examiner—Cris L. Rodriguez
Attorney, Agent, or Firm—Gary M. Nath; Harold L. Novick; Nath & Associates

[57] ABSTRACT

A hollow needle applicator for cartridged drugs etc has provision for automatic needle retraction after cartridge contents expression. Its drugs etc cartridge (125, 225, 325) can itself be at least partially accommodated bodily within a hollow piston actuator (145, 345), and will be released for retraction under bias (123, 3230 thereinto along with and by way of a piston rod (132, 332) first serving to operate contents (131, 331) discharge piston provision (130, 330) of the cartridge (125, 225, 335). The piston rod (132, 332) has deflectable arms (137, 337) that extend sideways further than side walling of the cartridge (125, 225, 335) and into temporary driving engagement with receiving formation(s) (147, 347) of the piston actuator (145, 345) until released by deflection of the arms (137, 337). The piston (132, 332) rod further has guiding formation(s) ((138, 338) extending into the hollow piston actuator (145, 345). The guiding formations (138, 338) and piston actuator (145, 345) are shown with temporary latching provisions (138P, 145G). A triggering ring (160) is also shown for releasing driving connection between the arms (137, 337) and the receiving formations (147, 147).

19 Claims, 4 Drawing Sheets

HOLLOW NEEDLE APPLICATOR FOR CARTRIDGED DRUGS

TECHNICAL FIELD

This invention relates to hollow needle applicators suitable for administering cartridged drugs etc.

In using the term "drugs etc" herein, there is no intention to limit application of this invention to drugs as such, even to antidote substances. This invention is seen as generally applicable to any usefully injectable substance; and to doing so into any appropriate receiver, i.e. whether or not that is tissue of a human or even animal subject.

BACKGROUND ART

Dangers of infection and cross-infection, much highlighted by the spread of AIDS, mean there is a need for hollow-needle devices as drugs etc applicators with automatic retraction and designed for single use only, i.e. designedly not lending themselves to re-use. This is, perhaps, particularly the case for cartridged drugs etc supplied as a one-dose item complete with applicator. Indeed, there have been many proposals over the years for such applicators, especially recently, but most are of doubtful practicality or of complex and costly construction, even both. We have, ourselves, made basic proposals (PCT application GB92/00652) for practical and low-cost single use hypodermic syringes (and body-fluid samplers) with automatic needle retraction on release of integral internal latching of an outer body part for a needle holder, including usable with cartridged drugs etc by use of a plunger element to release the needle holder latching after cartridge discharge.

We have made further proposals (PCT application no GB93/01004) for preloaded cartridged drugs etc applicators affording automatic needle retraction, including self-powering provisions for automatic needle extension before discharge of cartridge contents and needle retraction, and having deflectable angled piston rod arms for temporary drive stroke latching and then release deflection by cartridge engagement.

DISCLOSURE OF THE INVENTION

Objects of aspects of this invention include making further advantageous proposals for preloaded cartridged drugs etc applicators. Specifically, we are looking at achieving or improving one or more of certainty and/or reliability of operation and greater facility for automatic assembly.

The importance of certainty and/or reliability of operation for of drugs etc applicators is believed to be self-evident. However, it is also a matter of fundamental importance to facilitate automatic assembly; otherwise the essentials (for commercial success) of high production volumes at low unit cost will not be achievable.

According to one aspect of this invention, there is provided a hollow needle applicator for cartridged drugs etc having provision for automatic needle retraction after cartridge contents expression, wherein its drugs etc cartridge can itself be at least partially accommodated bodily within a hollow piston actuator and will be released for retraction under bias thereinto along with and by way of a piston rod first serving to operate contents discharge piston provision of the cartridge, the piston rod having deflectable arms that extend sideways further than side walling of the cartridge and into temporary driving engagement with receiving formation(s) of the piston actuator until released by deflection of the arms, wherein the piston rod further has guiding formation(s) always extending into the hollow piston actuator.

At least, indeed particularly but not necessarily exclusively, for assembly of more complex self-powering applicators with needle extension before discharge and retraction, it is further preferred that the guiding formation(s) further have temporary latching provision(s) relative to the hollow piston actuator.

This guidance aspect of this invention, including with said temporary latching, contributes substantially to facilitating automatic assembly, at least in connection with first associating the piston rod with the piston actuator, and whether or not for the purpose of further handling thereof as a subassembly. Moreover, as will become clear later herein, there are at least potential design and/or dimensional specification and/or operational advantages as well.

Preferred deflectable arms are angled both outwards and away from the cartridge, typically as extensions splayed from the piston rod behind the further guiding preferably latching formation conveniently provided at its end. A suitable piston rod structure is as a generally tubular member that can advantageously have an enlargement at its end, say of a divided type affording the deflectable arms and plural said guiding formations alternating in their extents about and longitudinally of the tubular piston rod. The deflectable arms are further preferably notched to bend as hinging for release purposes, rather than rely only on flexure.

Temporary latching for the or each further guiding formation may be by way of mutually engaging exterior provision, say beading or pip formations or grooving, and interior provision, say circumferentially extending grooving or beading, of the hollow piston actuator. Engagement between such provisions can coincide with and aid achieving desired location of the deflectable arms of the piston rod in the receiving formations of the piston actuator, but will not prevent retraction drive bias, at least after release deflection of those arms. Indeed, cooperating protecting formations can rely on engagement of the deflectable arms for latching location.

It will be appreciated that the particularly preferred division of a head enlargement to afford both of the arms and the guiding/latching formations as separated extensions from the body of the piston rod can inherently allow for sufficient inward deflection of the latter formations to facilitate smooth retraction of the piston rod and the drugs etc cartridge into the piston actuator. Moreover, retraction can be readily associated with advantageous gripping provision operative at or towards the end of retraction, say by the guiding/latching formations engaging on fin-like formations internally of the piston actuator.

According to another aspect of this invention, there is provided a hollow needle applicator for cartridged drugs etc having provision for automatic needle retraction after cartridge contents expression, wherein its drugs etc cartridge can itself be at least partially accommodated bodily within a hollow piston actuator and will be released for retraction under bias thereinto along with and by way of a piston rod first serving to operate contents discharge piston provision of the cartridge, the piston rod having deflectable arms that extend sideways further than side walling of the cartridge and into temporary driving engagement with receiving formations of the piston actuator until released by deflection of the arms, wherein a triggering ring serves in first engaging the deflectable arms to initiate retraction of the cartridge and piston rod after cartridge contents expression.

This triggering ring aspect of this invention has particular, but not necessarily exclusive, application to self-powering applicators with initial needle extension, where the user has no control over final applied release force. Reliance on the end of the cartridge for deflecting the arms to cause retraction is eliminated. This increases facilitation of use of whatever may be the most practical and desirable materials for the cartridge and the piston rod. There will be independence of significant possibility that the material of the cartridge, and/or the way its end is made, dressed or otherwise finished, might result in unusually high final release resistance, thus occasional malfunction; as we find can happen for simply cut glass cartridge tubing digging into some moulded plastics materials that are convenient for the piston rod, specifically at its intendedly deflectable arms. Indeed, the triggering ring can be made from a self-lubricating plastics material, say moulded from nylon or polypropylene to have also the inherent advantages of high accuracy arising from modern moulding techniques and practices. Moreover, as will become clear later, significant other and further advantages can be made available from using such a triggering ring, particularly where, as is preferred, the triggering ring is a sliding fit relative to the cartridge, i.e. the triggering ring is located in an outer body part of the applicator for the cartridge to pass slidingly through it.

A convenient location for the triggering ring, where the outer body part has a sectional reduction between one part housing the piston actuator (together with any associated drive spring released for expressing contents of the cartridge) and another part of reduced section housing the cartridge (and its needle if to be extended first) before its contents are expressed together with associated retraction spring, is within the one part adjacent the sectional reduction. Preferred seating is by way of accurately moulded internal stops or abutment ledges that contribute, along with accurately produced moulded triggering rings themselves, to assuring reliability of dosage discharged from the cartridge in causing triggering or retraction by deflection of the arms after a precise stroke of the piston rod and its associated piston.

A suitable and advantageous triggering ring structure is as of end-flanged tubular shape that will seat on its flange and have its other and relatively reduced end serve both for smooth engagement and operation of the deflectable arms of the piston rod, and for entry into the receiving formation(s) of the piston actuator; further preferably with a close match between its internal section and that of the piston actuator, or a slight under-sizing, so as, in any event, to afford assurance of forcing the deflectable arms clear of such receiving formation(s).

A particularly compact applicator with enhanced cartridge guidance results generally, i.e. with good centralisation of the cartridge. This can be of further advantage for applicators whose needles are to be extended before cartridge contents discharge, where the cartridge may first move from extending beyond to being within the extent of the triggering ring axially of the applicator.

The triggering ring can also serve as an assembly aid, say being an interference push fit into the outer body. Then, its interior cartridge-accommodating through-hole can usefully be a little smaller than the return spring and cartridge accommodating part of the outer body, and of the exterior of the return spring itself, so as to retain the latter when first loaded with little or no compression, i.e before engagement by the cartridge itself. Such push-type interference fit also contributes to shock-resistance of the assembled actuator. Moreover, provision of internal fins in the triggering ring can-produce a desirable degree of positive, basically frictional, grip on the cartridge, thereby further enhancing shock-resistance, including in an as-supplied state of the applicator. Such degree of cartridge gripping should be less than grip between the triggering ring and the interior walling of the outer body part, and less than the force exerted by the retraction spring as compressed and operative up to full desired retraction. It is, however, feasible for such grip to contribute usefully and advantageously in reducing initial kinetic energy of the piston rod and cartridge first arising at and after release of retraction spring provision, thus reducing shock at final stopping of the cartridge in the piston actuator. This is the case even where the piston actuator is provided with internal gripping fins operative in the final part of retractive movement of the piston rod and cartridge. Preferred finning of the triggering ring and/or the piston actuator for these purposes is of a flexing nature.

The above two aspects of invention are applicable in addition to the teaching of our PCT Application GB93/01004, and this reference thereto is intended to import hereto all relevant and useful contents of that patent specification, whether in relation to manually operated retractable hollow needle devices and retraction related latching provisions thereof, or to self-powered extending and retracting applicators, or to intermediate devices.

However, a particularly economic cartridge structure is envisaged herein, including as a further aspect of invention, namely a simple length of tube with a fixed needle holding closure at one end. This approach is of particular interest in relation to any device for handling drugs etc, i.e. for medical use, where materials approval requirements are especially strict and time-consuming to obtain. Accordingly, use of already approved materials, including glass, rubber, stainless steel and some plastics materials, is advantageous; and further advantageously enhanced by our present proposals.

One such proposal concerns glass, specifically a tube length closed at the needle end by an internally fitting short length of glass capillary tube into which a stainless steel needle is bonded. Such a fundamentally simple structure Is or would be equally viable and advantageous as applied to extrudable plastics materials approved or to be approved for medical use in relation to drugs etc. A plastics hub may, of course, be itself bonded to the needle, say for the usual purpose of fitting a needle sheath. An alternative using a bung can be mainly of elastomeric material, such as an approved rubber, suitably bonded into one end of tube and carrying a hollow needle, say by an intermediate moulded holder held captive in the bung. In a particularly preferred structure the bung is flanged at or near one of its ends to engage over the end of the tube with its main body part extending into the tube, and having a T-section cavity into its flanged end taking one headed end of a preferably a double-headed moulded needle holder sleeve whose preferred other head can serve to take a needle sheath. The T-section cavity can, with advantage, be blind and require to be pierced by the in-board end of a double-end-pointed needle.

In another drug etc cartridge, the closure is an end cap overfitting the tube. Such end cap can be engaged by capture members moved in a manually operated drugs etc applicator to release cartridge retraction drive means acting on the end cap. The end cap preferably further engages a tube bung of elastomeric material. The needle may be pointed at each end and passing through the end cap and the bung. The tube may further have an inner seal going from convex to concave to be pierced by the inboard end of the needle in readying the applicator for injection use.

BRIEF DESCRIPTION OF THE DRAWINGS

Exemplary specific implementation for this invention will now be described with reference to the accompanying diagrammatic drawings, in which.

BEST MODE FOR CARRYING OUT THE INVENTION

In FIGS. 1 to 4, the illustrated self-powered applicator 110 has an outer body component 111 that is generally tubular with parts 111A,B of different section, one smaller than the other. The smaller section part 111A extends from one end 113A, that is shown with internally returned necking 114 and orificed at 115 for passing a hollow needle 120, to a sectional transition 117. The larger section part 111B extends from the other end 113B to the shoulder 117, and has an end cap 119 shown snap-fitting by rib and groove formations 118R,G.

Figure 1:
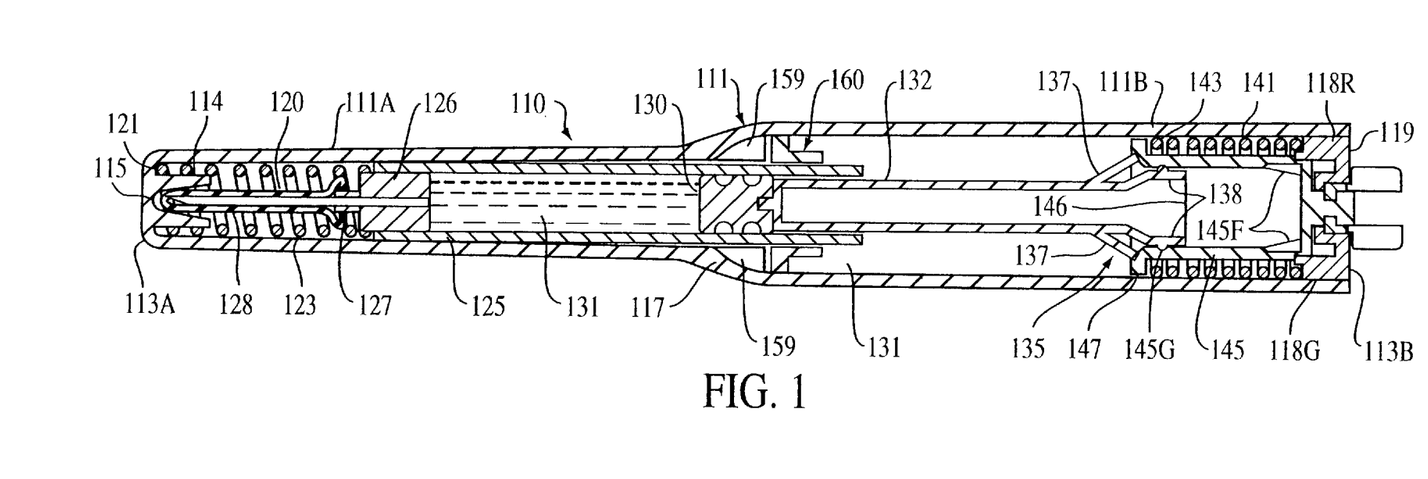
FIGS. 1 to 4 are outline longitudinal sectional views of a self-powered extending and retracting needle applicator in as-supplied, triggered and extended, discharged, and retracted states, respectively.

The smaller section body part 111A affords an annular seating recess 121 for a retraction bias spring 123 shown acting on a cartridge 125 provided with an end closure 126 carrying the hollow needle 120. The needle 120 is shown in FIG. 1 extending within the helical retraction spring 123 through a bonded-on hub 127 serving to hold a flexible needle-sealing sheath 128 within the annular wall 114 and part 129 (FIG. 4) of its end 113A between the orifice 115 and the annular wall 114 bounding retraction spring seating recess 121. The needle sheath 128 is shown (see FIG. 4) with a nose formation 128N to seat sealingly in the orifice 115, which represents potential advantage compared with such alternative provision as a separate septum disc in a retaining formation in and across the orifice 115. The annular wall 114 presents an internal taper away from the orifice 115, which, in cooperation with the preferred illustrated sheath 128 has a positive centralising effect for the needle 120, thus countering any risk of a thin and thus flexible needle getting out of registration with the orifice 115.

Figure 2:
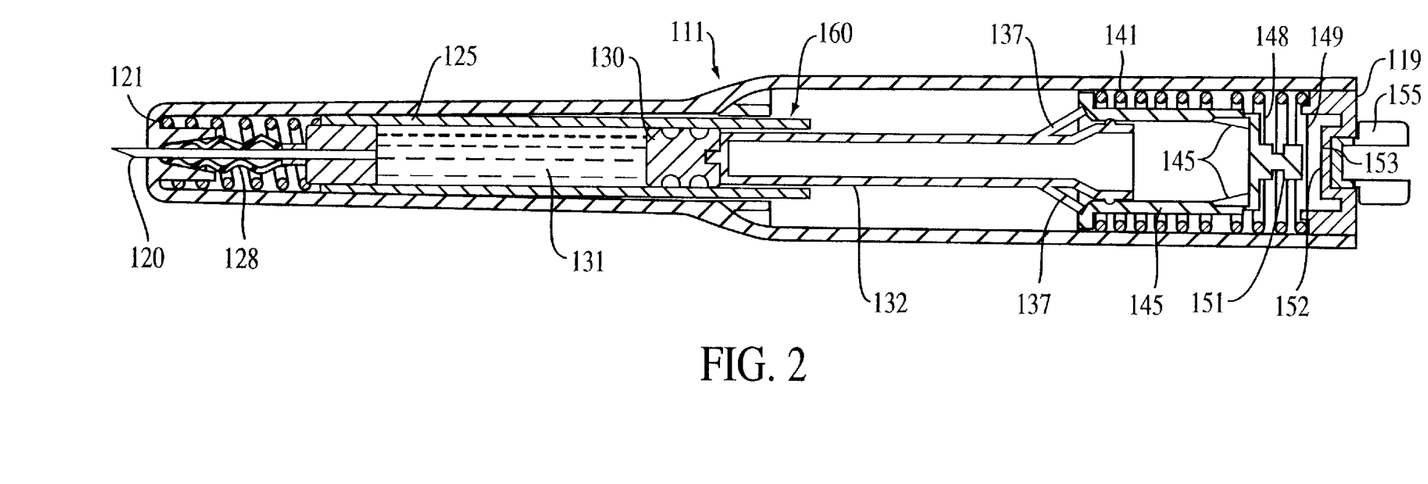
Figure 3:
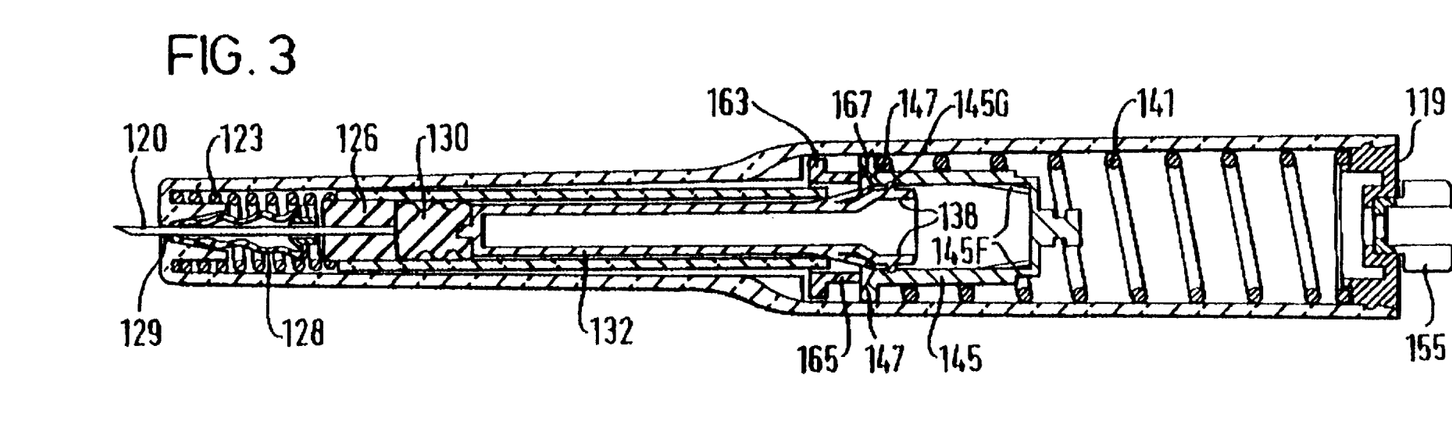
Figure 5:
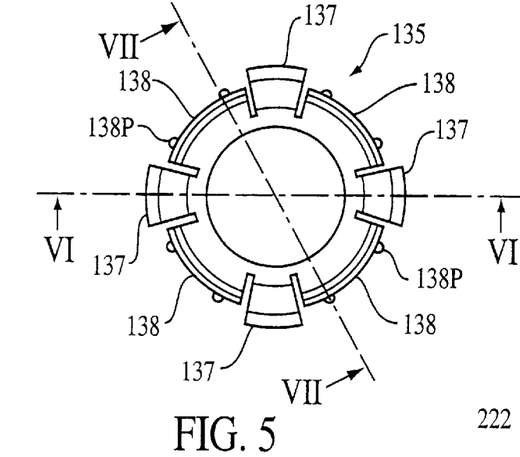
FIG. 5 is a detailed outline end view of part of a preferred piston rod.
Figure 6:
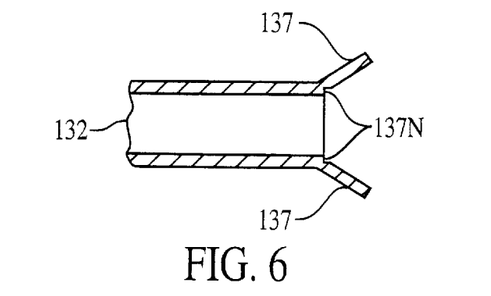
FIG. 6 is a sectional view of the FIG. 5 along VI—VI.
Figure 7:
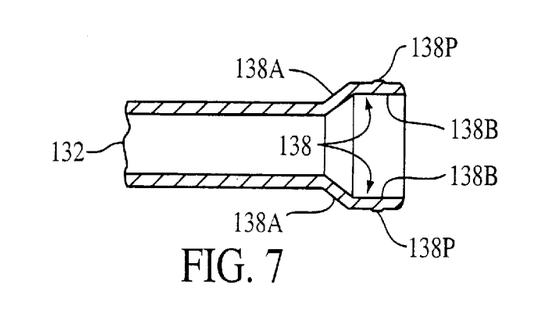
FIG. 7 is a sectional view of FIG. 5 along VII—VII.

The cartridge 125 has a piston 130 by which its contents (see volume referenced 131 of FIGS. 1 and 2) can be discharged through the needle 120 after penetration of the sealing sheath 128, shown in FIGS. 2 and 3 as involving concertina-like rucking-up. The piston 130 has a piston rod 132 of a length sufficient to accomplish a discharge stroke of the piston 130, i.e. to traverse the volume 131. The piston rod 132 extends away from the piston 130 to an end enlargement 135 (see also FIGS. 5 to 7) affording angled deflectable arms 137 going outwards beyond the outer confines of the cartridge 125, and also further guidance formations 138 for purposes to be described relative to FIGS. 5 and 7). Preferred deflection of the arms 137 (see FIG. 6) relies on an integral one-way hinge provision by way of notching 137N rather than on flexing of the arms 137 as such.

The larger section body part 111B houses a power drive spring 141 acting between the end cap 119 and exterior shoulder 143 of a cartridge piston actuator 145 that is shown hollow and capable of accepting the angled piston extension arms 137 when they are sufficiently squeezed inwards. However, open end 146 of the piston rod carrier or actuator 145 is shown wish a sloping ledge formation 147 to receive and be engaged by ends of the piston extension arms 137. Closed end 148 of the piston carrier or actuator 145 is shown (see FIG. 2) with an extension having a circumferential slot 149 forming a head 151 that can pass through an aperture 152 in the end cap 119 to be captured in and released from a key-hole slot 153 in a slide 155 associated with the end cap 119.

Figure 8:
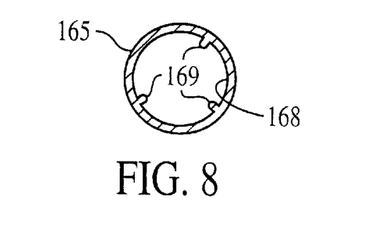
FIG. 8 is a detail outline end or sectional view of a preferred triggering ring.

Extending into the larger section body part 111B are stop or abutment ledge formations 159 for seating a triggering ring 160 shown with an end-flange 163 (FIG. 3) as its seating part. It is preferred that the flange 163 be an interference push-fit into the larger section body part 111B. From its end-flange 163, the triggering ring 160 extends at 165 to a free edge rim 167 that can engage in the receiving ledge formations 147 of the piston actuator as will be further explained below. The cartridge 125 can slide through the triggering ring 160, preferably (see FIG. 8) with a degree of friction by engagement with internal finning 169 of the triggering ring 160. Preferred finning 169 is of a flexing nature, say by way of angling between root and free parts thereof to each side of a crease or fold (not shown).

The outer body component 111 is readily injection moulded in one piece.

Reverting to the piston rod 132, a generally hollow tubular construction is preferred extending from a smaller blind and for securement at 131 to the piston 130 to an enlarged end affording the deflectable arms 137 and the guiding/latching formations 138 (see FIGS. 5 to 7) as alternating divided end leaves. The leaves representing the formations 138 go outwards at 138A then back to axial parallelism at 138B as a lose sliding fit in the interior of the hollow piston actuator 145. The formations 138 are further shown with exterior pips 138P capable of engaging, as a temporary fit for assembly and as-supplied states, in an internal groove 145G of the piston actuator 145 when the ends of the arm 131 seat in the receiving ledge formations 147. A less demanding provision, at least in terms of one-piece injection moulding requirements for the piston rod 132, is by way of internal beading formation for the piston actuator 145 (instead of the groove 145G), then with the pips 138P latching behind such beading and the ends of the deflectable arms 137 tight on the receiving ledging 147. Then, the pips 138P can be a simple slide fit in the interior of the piston actuator 145, say with slowing and gripping formations of the latter as indicated by fanning 145F in FIGS. 1 to 3.

In its as-supplied state, see FIG. 1, the device 110 has the piston carrier or actuator 145 captive to the end cap 119 so that the power drive spring 141 is compressed. The retraction spring 123 is partially extended to hold the cartridge 125 firmly located with the piston rod extension arms 137 seated at the ledging 147, at least for liquid contents of the cartridge effectively affording an hydraulic lock. The needle 120 is wholly retracted inside the body part 111A with its sheath none 128N preferably tight in the applicator needle orifice 115, as set by engagement of the piston rod arms 137 on the piston rod actuator ledging 147, the incompressible liquid contents of the cartridge 125, and sealing of the needle 120 by the sheath 128, albeit aided by preferred friction fit of the cartridge 125 in the triggering ring 160.

Releasing the piston rod actuator 145, by operating the slide 155, allows the power drive spring 141 first to move the cartridge 125 through the triggering ring 160, thus force the needle 120 through the sheath 128 and out of the orifice 115. At the same time the retraction spring 123 will be compressed with accompanying rucking up of the sheath 128, see FIG. 2 in which expression has also begun of the contents of the cartridge 125 through the extended needle 120. FIG. 3 shows such discharge expression completed with the piston 130 finally engaging the end plug 126 of the cartridge 125, and the triggering ring 160 having deflected the arms 137 to squeeze them together and out of the ledging 147.

Figure 4:
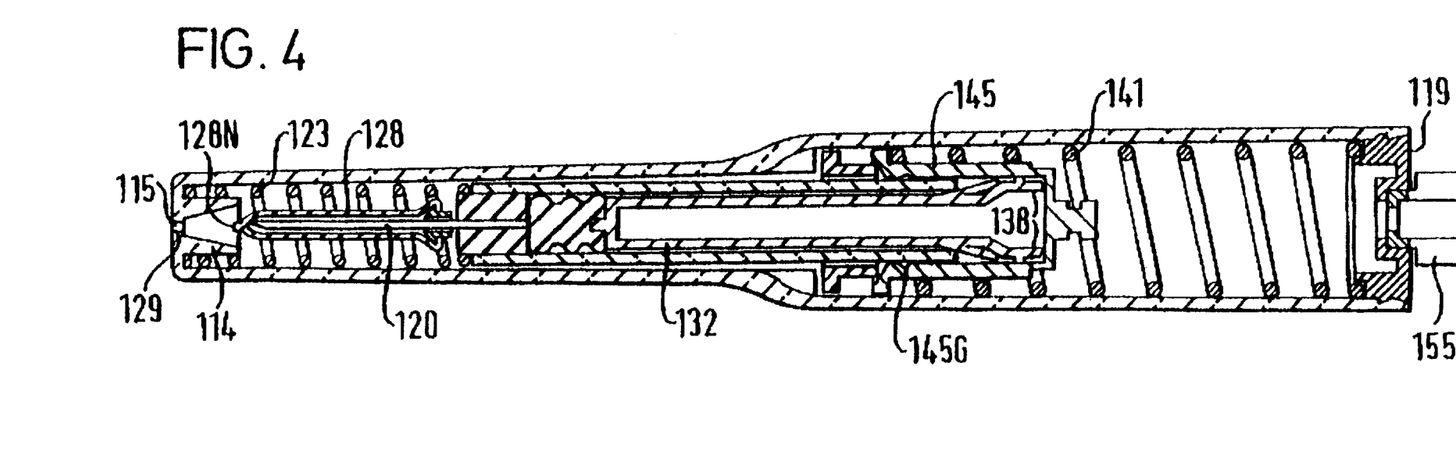

Thereafter the piston rod actuator 145 is arrested by the triggering ring 160 engaging the piston actuator ledging 147; and the retraction spring 123 will extend in driving the cartridge 125 (complete with needle 120 and the piston 130, piston rod 132 and extension arms 137) rearwardly, see FIG. 4, into the smaller body part 111A and the interior of the piston rod carrier or actuator 145 and through into the forward part of the larger section body part 111B. It will be appreciated that slowing and gripping provisions such as finning 145F may arrest the piston rod 132 before it reaches the position illustrated in FIG. 4, namely the end of the interior of the piston actuator 145. Preferred finning 145F is of a flexing nature, say by way of angling between root and free parts thereof to each side of a crease or fold (not shown).

It will be clear that the piston rod extension arms 137 are—for release from the piston actuator 145 to assure needle retraction—engaged by the end of the triggering ring 160 at a position outside the radial extent of the cartridge 125, thus further increasing leverage for release purposes (compared with relying only on the end of the cartridge 125).

Having substantial axial extents of guidance of the piston rod end at 138 in the piston rod actuator 145, and of the cartridge 125 in the triggering ring 160, provides advantages operationally as each contributes to smoothness and reliability of required movements of parts of the illustrated applicator. Having provisions, preferably integral formations, with progressively increasing gripping characteristics for the piston rod 132 in its retraction into the piston actuator 145 reduces risks of unwanted bouncing effects. Having friction between the cartridge 125 and the triggering ring 160 assists with shock resistance, both as-supplied and in operation.

Having the piston rod 132 and the piston actuator 145 latch together as a first state contributes significantly to aiding assembly, particularly facilitation of automatic assembly. Having a force-fit for the triggering ring 160 in the outer body part 111B also has assembly aiding connotations, perhaps particularly when its internal bore 168 (or at least as added to by finning provisions 169) is smaller than the exterior of the retraction spring 123, thus allowing capture of the latter as an assembly step.

Indications in FIGS. 1 to 4 for the cartridge 125 are in terms of a simple tube closed at one end by a plug 126 carrying the needle 120. The plug 126 is even of a tubular nature, so cartridge construction can come down to the matter of suitable bonding together on the one hand the needle in the bore of the tubular plug 126, and on the other band the tubular plug 126 in the end of the main tube of the cartridge. Glass main tube and glass capillary tube for the plug 126 are good candidates amongst materials already carrying approvals for medical use with drugs etc.

Figure 9:
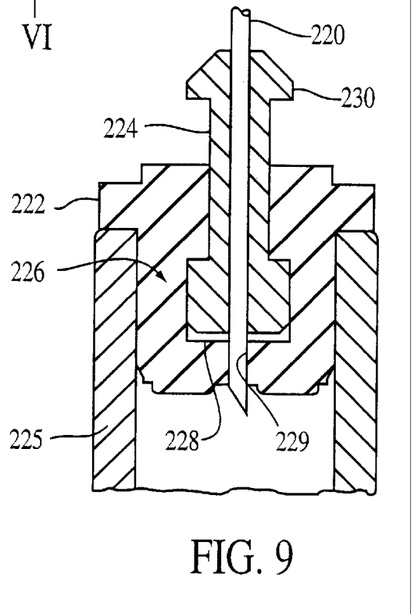
FIGS. 9 and 9A are detail outline longitudinal sectional and end views of the needle-carrying end of a preferred drugs etc cartridge.
Figure 9A:
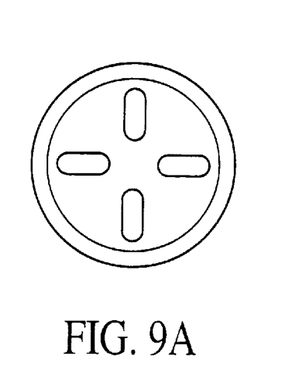

An alternative construction is, however, shown in FIGS. 9 and 9A. Again, a simple length of tube (which can be glass) is shown at 225, but here closed off by a rubber bung 226 shown with preferred flanging 222 engaging over the end of the tube 225 and readily sealingly secured in place using proprietary bonding agent wiped over at least the flange-adjacent surface of the bung. However, prior to such securement, the bung 226 will have been fitted with a hub 224 component serving as a holder for the hollow needle 220. Such fitment is made easy by way of a T-section cavity 228 in the bung 226 having a shape conforming to that of the hub 224, specifically end-enlargement of the hub 224, so that there is a highly positive capture fitting, perhaps especially after further securement of the bung 226 into the main tube 225. The hub 224 can be of autoclavable moulded plastics (e.g. polycarbonate or polyethylene) and the needle may be bonded in before offering the hub 224 to the bung 225. The needle is, of course, shown passing through a hole 229 from the cavity 228 of the bung into communication with the interior of the main tube 225. Preferably, the bung 225 is made blind below the cavity 228, and the hole 229 is made by piercing using a double-end-pointed needle 220. The enlargement 230 of the other end of the hub 224 will serve for securement of a needle sheath.

Whilst a fully self-powered needle extending and retracting applicator is illustrated, this invention is also applicable to other hollow needle drugs etc delivery devices. For example, a manually operated version of what is illustrated could omit the drive spring 141 and have a much simpler end construction by way of finger grip flange provisions on the outer body part 111B and a plunger extension for the piston actuator 145. Omission of needle extension is also readily done for manual or self-powered versions, simply by shortening the smaller section body part 111A and installing its retraction spring compressed, say by installation of the push-fit triggering ring.

Figures 10, 11:
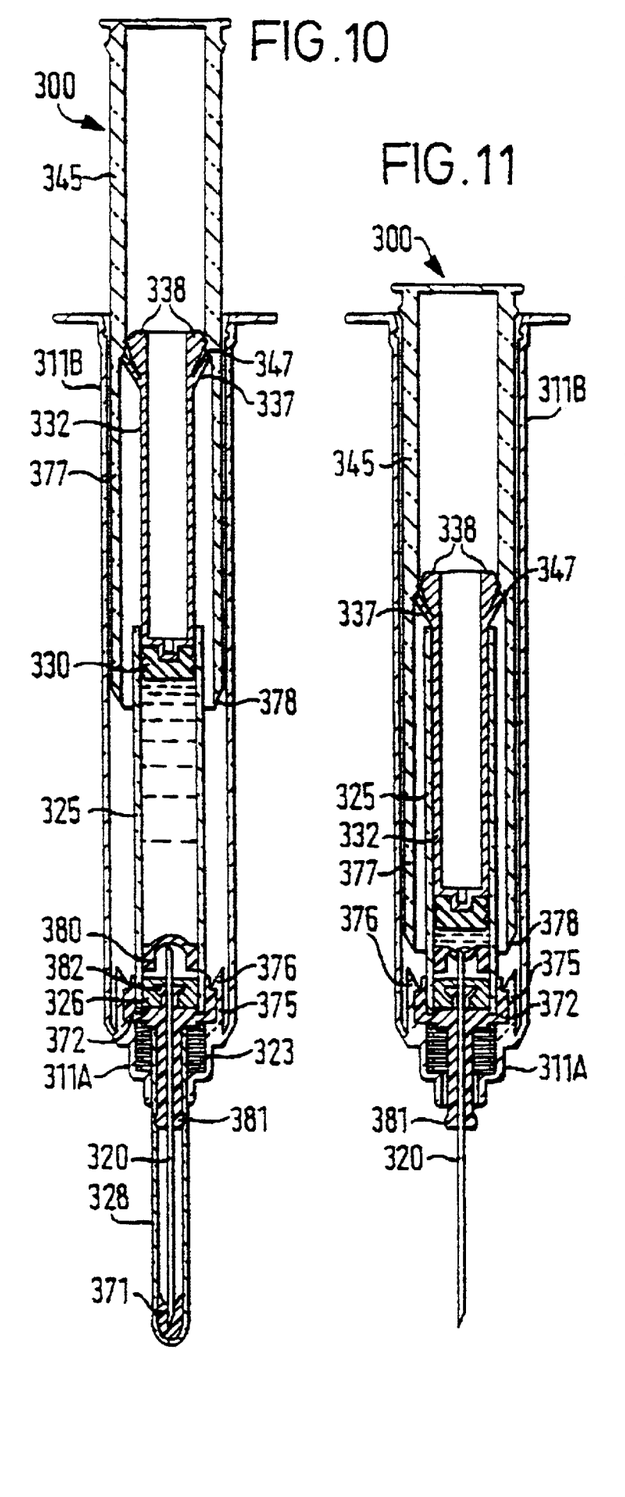
FIGS. 10, 11 and 12 are outline longitudinal sectional views of a manually operated applicator with automatic needle retraction.
Figure 12:
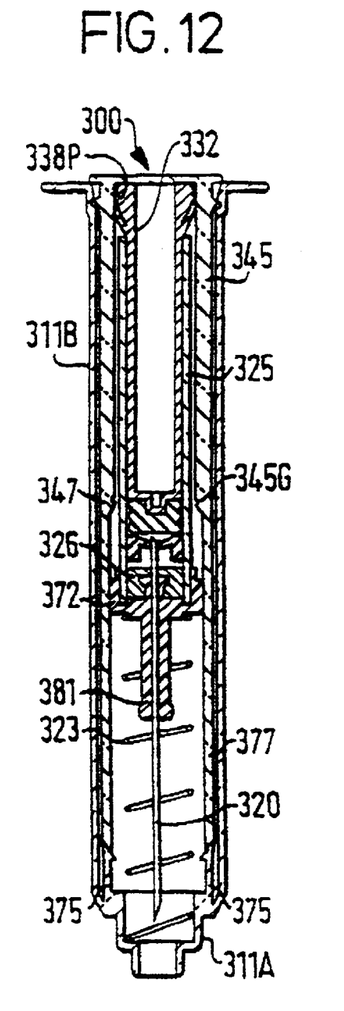

FIGS. 10 to 12 show a manually operated applicator for drugs etc, and equivalent parts to those of FIGS. 1 to 4 have references advanced by 200. Before use, the needle 320 extends from much shorter forward outer body chamber shown at 311A housing needle retraction spring 323, and has external protective sheath 328 and a terminating needle closure seal 371. Extending rearward into main outer body chamber shown at 311B are integrally moulded latching members 375 having accommodation(s) for outward flexing to disengage end teeth 376 from capture retention of the drugs etc cartridge 325 at outer rim of its end cap 372 also serving as a holder or hub for the needle 320. These latching members are generally as in our PCT application GB92/00612 and FIGS. 1–4 of our PCT application GB93/01004. Manually operated hollow piston actuator 345 extends at 377 well beyond receiving formations 347 for arms 337 to chamfered rim 378 smoothly to release sloping teeth 376, thus flexing members 375 and releasing needle retraction spring 323 at end of actuator movement and cartridge discharge. The tubular piston rod 332 has guidance formations 338 within the hollow actuator 345, along with pips 338P and cooperating grooving 345G in the piston actuator 345.

The cartridge end cap 372 is acted on directly by the retraction spring 323; and is shown with needle 320 traversing forward extension 381 for the sheath 328 and rearward extension 382 into resilient cartridge end plug 326 through which double-ended needle 320 is also shown passing. The cartridge 325 is further shown with an optional inverting inner seal 380 that will go from rearwardly convex and intact to concave and pierced by the needle 320 at a first movement of the actuator 345 in readying for injection of drug etc.

This embodiment represents a low-cost pre-loaded syringe 300 to be supplied in a sterilised package for use primarily by health-care professionals, but with safety from needle-stick risks after administering contents to a patient by way of automatic needle retraction and effective safe encapsulation. The cartridge can be of borosilicate glass tube with rubber closures, or such other materials as have or get appropriate drug-compatibility approvals. Use is simply by removing a syringe 300 from its package, first manual depression of the piston actuator 345 enough to invert the isolator seal 380 for penetration by the needle 320, removal of the needle sheath 328 conveniently complete with preferably snapped-in fitting terminating closure 371, second manual depression of the piston actuator plunger 345 to adjust for desired dose, and then normal insertion into the patient for administration of that dose.

A version is feasible and envisaged that will enable user choice of needle, say with cartridge end cap 372 apertured and formed cooperatingly to take the needle of choice, say push-fitting for any suitable needle holder or hub.

INDUSTRIAL APPLICABILITY

Filling and assembly is advantageously simple and suited to high-speed automation. A needle assembly is readily made up by light-cure resin fixing of the needle 320 in the cartridge end cap 372, snap-fitting cartridge end plug 326 onto the cap 372 and the needle closure 371 into the preferably rigid needle sheath 328, and snap fitting the needle sheath 328 onto the cartridge end cap 372. This needle assembly is the readily light-cure resin bonded into the glass tube of the cartridge 320, which may carry dose scale marking visible through preferably see-through syringe outer body part 311B. The optional isolator seal 380 will then be fitted if required, and the empty cartridge 325 sterilised. After filling of the sterile cartridge 325 and closing by the piston 330, any required terminal sterilising of the filled cartridge is done. For the syringe body itself, the retraction spring 323 is first fitted, followed by the filled cartridge 320 pressed home past the integral latching members/teeth 375/376 thus compressing the retraction spring 323. The piston rod 332 will snap-fit into the end of the piston actuator 345 if pips/grooves 338P/343G are provided, and the resulting assembly readily fitted into the syringe body with automatic location of the piston rod 332 in the cartridge piston 330. The whole can then be labelled and packaged, typically into a suitable pouch or box.

I claim:

1. A hollow needle applicator for cartridged drugs etc of a type affording automatic needle retraction after cartridge contents expression, the applicator comprising a hollow elongate body having a top portion and bottom portion and that, at least in operation, houses a hollow drugs etc cartridge biased toward the bottom portion of the body and having side walling slidable in the body and a discharge piston with a piston rod extending out of the cartridge as such longitudinally of the body, and a hollow piston actuator biased toward the top portion of the body and slidable in the body and capable of at least partially bodily accommodating the cartridge as well as the piston rod, the piston rod having deflectable arms that extend sideways further than the side walling of the cartridge, the piston actuator having receiving formations with which the deflectable arms make temporary driving engagement until the deflectable arms are engaged and released during bias driven movement of the piston actuator toward the bottom portion of the body before a bias driven movement of the cartridge toward the bottom portion of the body, and the piston rod having a guiding formation extending into the hollow piston actuator.

2. The hollow needle applicator according to claim 1, wherein said guiding formation is located on the piston rod toward an open end of the hollow piston actuator.

3. The hollow needle applicator according to claim 2, wherein the deflectable arms are angled both outwards and away from the cartridge as extensions splayed from the piston rod behind the guiding formation.

4. The hollow needle applicator according to claim 1, wherein the piston rod comprises a generally tubular member having enlargement of its end to fit in the hollow piston actuator, the enlargement being divided in affording the deflectable arms and a plurality of said guiding formations alternating in their extents about and longitudinally of the tubular piston rod.

5. The hollow needle applicator according to claim 1, wherein the deflectable arms are notched to bend as hinging for release purposes rather than rely only on flexure.

6. The hollow needle applicator according to claim 1, further comprising a cooperating temporary latching provision of the guiding formation and the hollow piston actuator.

7. The hollow needle applicator according to claim 6, wherein the temporary latching provision of the guiding formation comprises exterior means thereof mutually engaging with the interior provision of the hollow piston actuator simultaneously with the driving engagement of the deflectable arms of the piston rod in the receiving formation of the piston actuator.

8. The hollow needle applicator according to claim 1, wherein the hollow piston actuator has an internal gripping provision near an end thereof and is operative at or towards the end of retraction by engaging the guiding formation.

9. The hollow needle applicator according to claim 1 wherein the drug etc cartridge for applicator has a simple length of constant section tube with a fixed needle holding closure at one end, both the tube and the closure being of materials meeting relevant medical use approval requirements.

10. The hollow needle applicator according to claim 9, wherein the tube is glass closed at the needle end by an internally fitting short length of glass capillary tube into which a stainless steel needle is bonded.

11. The hollow needle applicator according to claim 9, wherein the closure is a bung of elastomeric material bonded into one end of the tube and carrying a hollow needle holder held captive in the bung, the holder being a sleeve headed at both ends, the bung being end-flanged to engage over the end of the tube with its main body part extending into the tube and having a T-section cavity into its flanged end taking one headed end of the holder sleeve, the other headed end of the holder sleeve serving to take a needle sheath.

12. The hollow needle applicator according to claim 11, wherein said needle is a double-end-pointed needle having an in-board end and an out-board end, and the T-section cavity is blind until pierced by the in-board end of said needle.

13. The hollow needle applicator according to claim 9, and further including capture members and a tube bung; and wherein the closure is an end cap overfitting the tube to be engaged by said capture members moved to release cartridge retraction drive means acting on the end cap, the end cap engaging said tube bung of elastomeric material, the needle being pointed at each end and passing through the end cap and the bung, the tube further having an inner seal going from convex to concave to be pierced by the inboard end of the needle in readying the applicator for injection use.

14. The hollow needle applicator according to claim 1, wherein the deflectable arms are angled both outwards and away from the cartridge as extensions splayed from the piston rod behind the further guiding formation.

15. A hollow needle applicator for cartridged drugs etc which affords automatic needle retraction after cartridge contents expression, the applicator comprising a hollow elongate body having a top portion and a bottom portion and that, at least in operation, houses a hollow drugs etc cartridge biased toward the bottom portion of the body and having side walling slidable in the body and a discharge piston with a piston rod extending out of the cartridge as such longitudinally of the body, and a hollow piston actuator biased toward the top portion of the body and slidable in the body and capable of at least partially bodily accommodating the cartridge as well as the piston rod;

the piston rod having deflectable arms that extend sideways further than the side walling of the cartridge, the piston actuator having receiving formations with which the deflectable arms make temporary driving engagement until the deflectable arms are engaged and released during bias driven movement of the piston actuator toward the bottom portion of the body before bias driven movement of the cartridge toward the bottom portion of the body, and a triggering ring about the cartridge to serve in first engaging the deflectable arms to initiate retraction of the cartridge and piston rod after cartridge contents expression.

16. The hollow needle applicator according to claim 15, wherein the triggering ring is of a moulded self-lubricating plastics material.

17. The hollow needle applicator according to claim 15, wherein the body has an outer body part, a sectional reduction between a rearward chamber housing at least the piston actuator and a forward chamber of reduced section housing at least a needle retraction spring, the triggering ring being a sliding fit relative to the cartridge, and being located in the outer body part of the applicator for the cartridge to pass slidingly through it at the sectional reduction, and the triggering ring being seated at integrally moulded internal stops or abutment ledges of the outer body part.

18. The hollow needle applicator according to claim 15, wherein the triggering ring is of end-flanged tubular shape that will seat on its flange and has its other end relatively reduced to serve both for smooth engagement and operation of the deflectable arms of the piston rod, and for entry into the receiving formation of the piston actuator, the needle being extended before cartridge contents discharge and the cartridge first moving from extending beyond to being within the axial extent of the triggering ring.

19. The hollow needle applicator according to claim 15, wherein the triggering ring is an interference push fit into the outer body, and has internal fins for a degree of positive grip on the cartridge, such grip being less than the grip between the triggering ring and the interior walling of the outer body part and less than the force exerted by the retraction spring as compressed and operative up to full desired retraction, but enough to contribute in reducing initial kinetic energy of the piston rod and cartridge arising from needle retraction spring release.

\* \* \* \* \*